(12) United States Patent
Soejima et al.

(10) Patent No.: US 10,408,905 B2
(45) Date of Patent: Sep. 10, 2019

(54) MAGNETIC RESONANCE IMAGING APPARATUS AND TRANSMISSION CONTROL METHOD

(71) Applicant: TOSHIBA MEDICAL SYSTEMS CORPORATION, Otawara-Shi, Tochigi-Ken (JP)

(72) Inventors: Kazuyuki Soejima, Nasushiobara (JP); Haruki Nakamura, Nasushiobara (JP); Takuma Kawai, Nasushiobara (JP); Kazuya Okamoto, Saitama (JP)

(73) Assignee: TOSHIBA MEDICAL SYSTEMS CORPORATION, Otawara-Shi, Tochigi-Ken (JP)

( * ) Notice: Subject to any disclaimer, the term of this patent is extended or adjusted under 35 U.S.C. 154(b) by 0 days.

(21) Appl. No.: 15/820,718

(22) Filed: Nov. 22, 2017

(65) Prior Publication Data

US 2018/0106878 A1 Apr. 19, 2018

Related U.S. Application Data

(63) Continuation of application No. 14/162,094, filed on Jan. 23, 2014, now Pat. No. 9,857,445, which is a (Continued)

(30) Foreign Application Priority Data

Sep. 25, 2012 (JP) .................................. 2012-211363

(51) Int. Cl.
*G01V 3/00* (2006.01)
*G01R 33/54* (2006.01)
(Continued)

(52) U.S. Cl.
CPC ............ *G01R 33/543* (2013.01); *A61B 5/055* (2013.01); *G01R 33/36* (2013.01);
(Continued)

(58) Field of Classification Search
CPC .................................................... G01R 33/543
(Continued)

(56) References Cited

U.S. PATENT DOCUMENTS

| 4,685,468 A | 8/1987 | MacOvski |
| 9,625,541 B2 * | 4/2017 | Fontius ................ G01R 33/288 |

(Continued)

FOREIGN PATENT DOCUMENTS

| JP | 5-23315 | 2/1993 |
| JP | 2004-526547 | 9/2004 |

(Continued)

OTHER PUBLICATIONS

English Translation of International Preliminary Report on Patentability dated Mar. 31, 2015 for Application No. PCT/JP2013/075082 (4 pages).

(Continued)

*Primary Examiner* — Louis M Arana
(74) *Attorney, Agent, or Firm* — Nixon & Vanderhye P.C.

(57) ABSTRACT

According to one embodiment, a magnetic resonance imaging apparatus provided with a plurality of transmission channels includes a signal processing unit and a control unit. The signal processing unit acquires a radio frequency magnetic field emitted from each of the plurality of transmission channels through a receiver coil mounted on an object and measure a phase of the radio frequency magnetic field. The control unit determines a phase difference between the plurality of transmission channels based on the phase of the radio frequency magnetic field of each of the plurality of transmission channels measured by the signal processing unit. The control unit controls a phase of a radio frequency pulse inputted to each of the plurality of transmission channels, based on the phase difference.

6 Claims, 6 Drawing Sheets

Related U.S. Application Data continuation of application No. PCT/JP2013/075082, filed on Sep. 18, 2013.

(51) Int. Cl.
*A61B 5/055* (2006.01)
*G01R 33/36* (2006.01)
*G01R 33/561* (2006.01)
*A61B 5/00* (2006.01)

(52) U.S. Cl.
CPC ........ *G01R 33/3607* (2013.01); *A61B 5/0037* (2013.01); *G01R 33/5612* (2013.01)

(58) Field of Classification Search
USPC ........................................ 324/309, 318, 322
See application file for complete search history.

(56) References Cited

U.S. PATENT DOCUMENTS 9,857,445 B2 * 1/2018 Soejima ............... G01R 33/543
2004/0155656 A1   8/2004 Leussler et al.
2007/0273377 A1 * 11/2007 Yang .................. G01R 33/3415
                                                              324/318
2012/0238861 A1   9/2012 Gebhardt

FOREIGN PATENT DOCUMENTS

| JP | 2006-141774 | 6/2006 |
|---|---|---|
| JP | 2011-131045 | 7/2011 |
| JP | 2012-24306 | 2/2012 |
| JP | 2012-239737 | 12/2012 |

OTHER PUBLICATIONS

International Search Report for PCT/JP2013/075082 dated Dec. 24, 2013 (3 pages).

P.P. Stang et al., Vector Iterative Pre-Distortion: "An Auto-calibration Method for Transmit Arrays", Proc, Intl, Soc. Mag. Reson. Med 17, Apr. 2009, p. 396.

M.G. Zanchi et al., "Frequency Offset Cartesian Feedback Control System for MRI Power Amplifier", Proc. Intl. Soc. Mag. Reson. Med. 17, 2009, p. 399.

* cited by examiner

MAGNETIC RESONANCE IMAGING APPARATUS AND TRANSMISSION CONTROL METHOD

CROSS-REFERENCE TO RELATED APPLICATIONS

This application is a continuation of application Ser. No. 14/162,094, filed Jan. 23, 2014 which is a continuation of PCT/JP2013/75082, filed on Sep. 18, 2013, and the PCT application is based upon and claims the benefit of priority from Japanese Patent Application No. 2012/211363, filed on Sep. 25, 2012, the entire contents of which are incorporated herein by reference.

FIELD

Embodiments described herein relate generally to a magnetic resonance imaging apparatus and transmission control method.

BACKGROUND

A transmitter coil of a magnetic resonance imaging (MRI) apparatus is designed to accept as input a radio frequency (RF) pulse and emit a radio frequency (RF) magnetic field (B1) to an object.

Some MRI apparatus have plural transmission channels. It is important for this type of MRI apparatus to perform control such that the RF pulse inputted to each transmission channel will have a desired amplitude and phase.

However, in calibrating the amplitude and phase inputted to each transmission channel, a method which uses the amplitude and phase of a signal outputted by a unit configured to generate transmit pulses cannot take into consideration the influence caused by all transmission paths of the transmit pulses. For example, the influence of a signal cable running from the unit to the transmission channel is not reflected.

Consequently, it is not possible to keep track of amplitude losses and phase shifts of the RF pulse accurately, which could disable B1 distortion correction, resulting in increased RF strength. Also, if adjustments are made using a network analyzer or the like to correct the phase shifts, the adjustments will take time, resulting in greatly reduced convenience.

Also, when the amplitude and phase of input to each transmission channel are calibrated using a method which uses output from an RF measurement pickup coil installed in a gantry aside from a receiver coil, this means that there are three types of coils in the gantry: the transmitter coil, receiver coil, and pickup coil. In this case, it becomes difficult to make adjustments due to interference among the coils. Also, increases in the number of parts will increase a failure rate, size, and cost.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

An embodiment of a magnetic resonance imaging apparatus and transmission control method according to the present invention will be described with reference to the accompanying drawings.

In general, according to one embodiment, a magnetic resonance imaging apparatus provided with a plurality of transmission channels includes a signal processing unit and a control unit. The signal processing unit acquires a radio frequency magnetic field emitted from each of the plurality of transmission channels through a receiver coil mounted on an object and measure a phase of the radio frequency magnetic field. The control unit determines a phase difference between the plurality of transmission channels based on the phase of the radio frequency magnetic field of each of the plurality of transmission channels measured by the signal processing unit. The control unit controls a phase of a radio frequency pulse inputted to each of the plurality of transmission channels, based on the phase difference.

Figure 1:
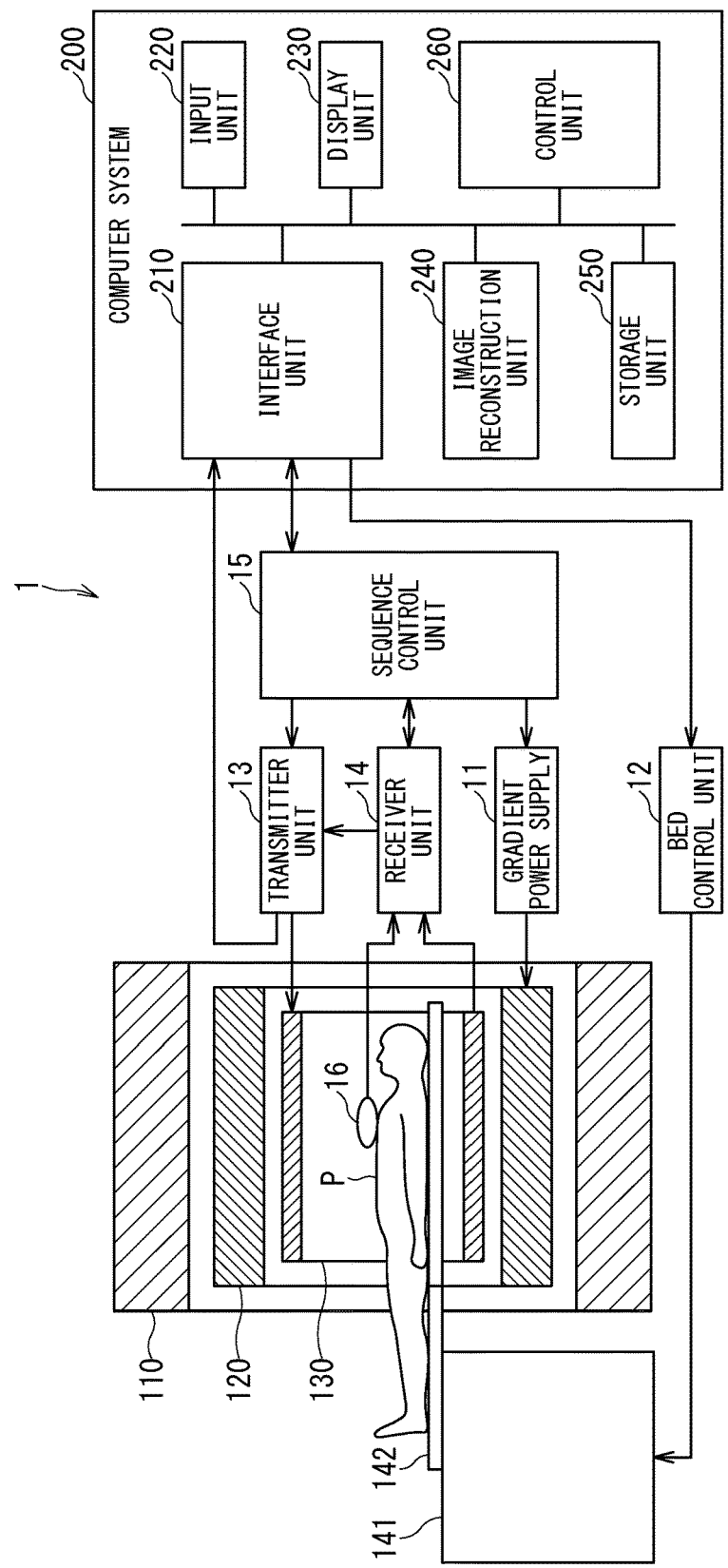
FIG. 1 is a block diagram showing a configuration example of an MRI apparatus according to an embodiment of the present invention.

FIG. 1 is a block diagram showing a configuration example of an MRI apparatus 1 according to an embodiment of the present invention.

A static magnet 110 formed into a hollow cylindrical shape generates a uniform static magnetic field in an internal space using an electric current supplied from a magnetostatic power supply (not shown). The static magnet 110 is made, for example, of a permanent magnet or superconductive magnet. A gradient coil 120 formed into a hollow cylindrical shape generates a gradient magnetic field in an internal space. Specifically, the gradient coil 120 is placed inside the static magnet 110 and configured to generate the gradient magnetic field by being supplied with an electric current from a gradient power supply 11 described later.

An RF coil 130 is a combined transmitter-receiver coil disposed in an opening of the static magnet 110, facing an object P and is configured to generate RF magnetic fields by being supplied with RF pulses from a transmitter unit 13. Also, the RF coil 130 receives a magnetic resonance signal released from hydrogen atomic nuclei of the object P as a result of excitation and provides the magnetic resonance signal to a receiver unit 14.

The RF coil 130 generates the RF magnetic fields on a multichannel basis under the control of the transmitter unit 13. The RF coil 130 is, for example, a QD (Quadrature Detection) coil, a saddle coil, a birdcage coil, or the like. In the following description, it is assumed by way of example that the RF coil 130 generates RF magnetic fields using four transmission channels CH1, CH2, CH3, and CH4.

A bed apparatus 141 includes a table top 142 on which the object P is mounted. The table top 142 with the object P mounted is inserted into a cavity (imaging port) of the RF coil 130. Usually, the bed apparatus 141 is installed such that a longitudinal direction will be parallel to a center axis of the static magnet 110.

The gradient power supply 11 supplies an electric current to the gradient coil 120. A bed control unit 12, which is an apparatus configured to control the bed apparatus 141 under the control of a control unit 260 described later, moves the table top 142 in the longitudinal and vertical directions by driving the bed apparatus 141.

A computer system 200 performs overall control of the MRI apparatus 1, collects MR signal data, reconstructs images, and so on.

An interface unit 210 controls input and output of various signals exchanged with a sequence control unit 15. For example, the interface unit 210 transmits sequence information to the sequence control unit 15 and receives MR signal data from the sequence control unit 15. Upon receiving the MR signal data, the interface unit 210 stores the received MR signal data in a storage unit 250. Also, upon receiving feedback information from the transmitter unit 13, the interface unit 210 inputs the received feedback information to the control unit 260.

An input unit 220 accepts various actions and information inputs from an operator. Being equipped with a pointing device such as a mouse or trackball, a keyboard, and the like, the input unit 220 provides a GUI (Graphical User Interface) to the operator of the MRI apparatus 1 in conjunction with a display unit 230 to accept the various actions. The display unit 230 displays various information such as image data under the control of the control unit 260 described later. A display device such as a liquid crystal display is available for use as the display unit 230.

An image reconstruction unit 240 reconstructs an MRI image by performing a reconstruction process such as a Fourier transform on the MR signal data stored in the storage unit 250 and stores the reconstructed MRI image in the storage unit 250.

The storage unit 250 stores the MR signal data received by the interface unit 210, the MRI image stored by the image reconstruction unit 240, and other data used in the MRI apparatus 1. Also, the storage unit 250 according to the present embodiment stores transmission conditions such as a phase difference between the RF pulse to be transmitted to the transmission channel CH1 of the RF coil 130 and RF pulse to be transmitted to the transmission channel CH2 and power (amplitudes) of the two RF pulses. The storage unit 250 is, for example, a RAM (Random Access Memory), a semiconductor memory element such as a flash memory, a hard disk, an optical disc, or the like.

The control unit 260 generally controls the MRI apparatus 1 by controlling all the components described above. For example, the control unit 260 generates sequence execution data based on imaging conditions entered by the operator via the input unit 220, transmits the generated sequence execution data to the sequence control unit 15, and thereby controls scans on the MRI apparatus 1. The control unit 260 is, for example, an integrated circuit such as an ASIC (Application Specific Integrated Circuit) or FPGA (Field Programmable Gate Array), or an electronic circuit such as a CPU (Central Processing Unit) or MPU (Micro Processing Unit).

Figure 2:
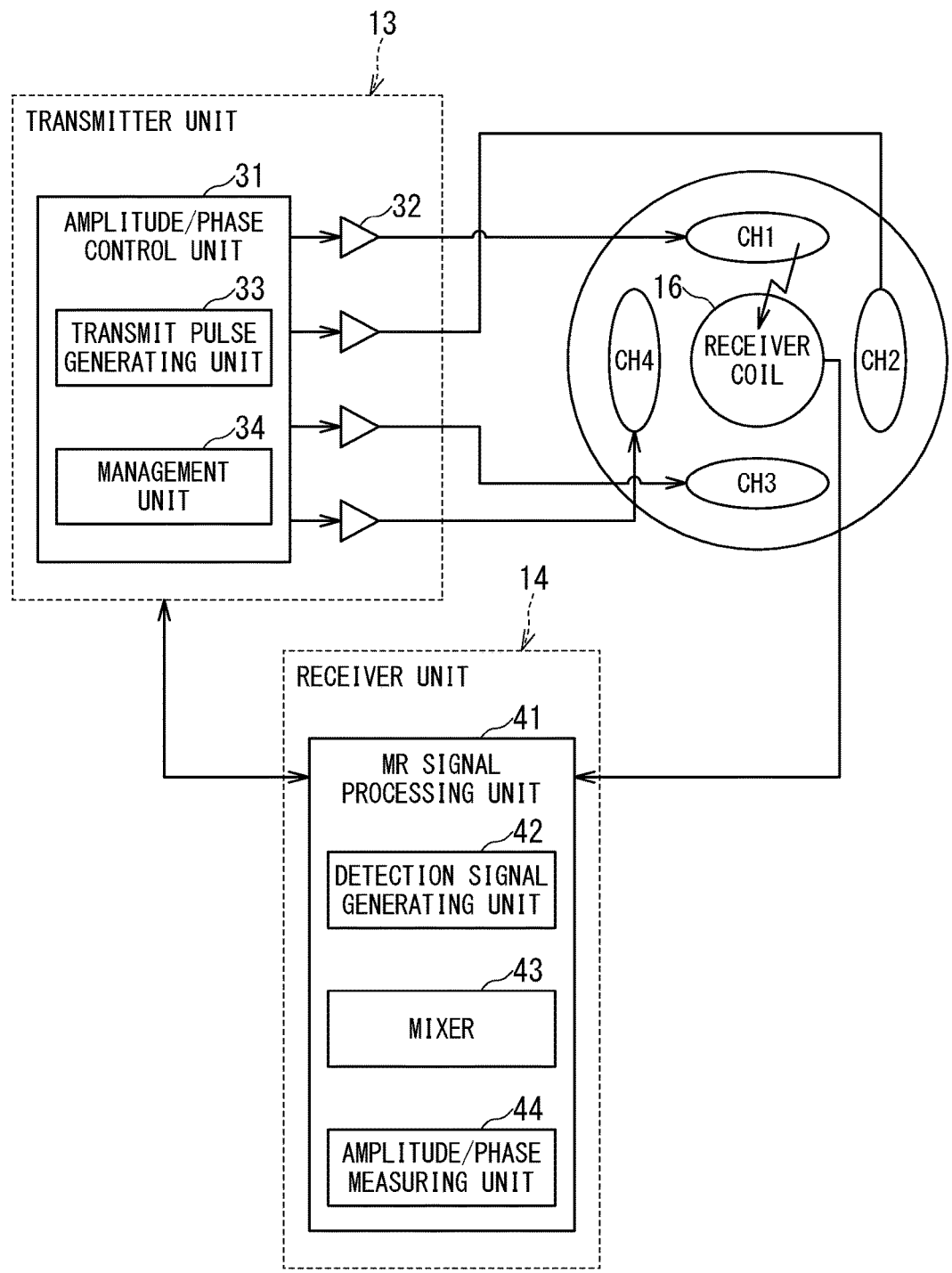
FIG. 2 is an explanatory diagram showing an example of relationships among the transmitter unit, the receiver unit, the plural transmission channels CH1 to CH4, and the receiver coil.

FIG. 2 is an explanatory diagram showing an example of relationships among the transmitter unit 13, the receiver unit 14, the plural transmission channels CH1 to CH4, and the receiver coil 16.

The transmitter unit 13 transmits an RF pulse corresponding to Larmor frequency to the RF coil 130 under the control of the sequence control unit 15. Specifically, the transmitter unit 13 includes an amplitude/phase control unit 31 and an RF amplifier 32.

The amplitude/phase control unit 31 includes a transmit pulse generating unit 33 and a management unit 34.

The transmit pulse generating unit 33 includes an oscillation unit, a phase selection unit, a frequency conversion unit, and an amplitude modulation unit. Under the control of the management unit 34, the transmit pulse generating unit 33 generates RF pulses to be inputted to the respective transmission channels CH1 to CH4 while adjusting the amplitudes and phases of the RF pulses on a channel by channel basis.

The oscillation unit generates a radio frequency signal with a resonance frequency unique to a target atomic nucleus in a static magnetic field. The phase selection unit selects a phase of the generated radio frequency signal. The frequency conversion unit converts the frequency of the radio frequency signal outputted from the phase selection unit. The amplitude modulation unit modulates the amplitude of the radio frequency signal outputted from the frequency conversion unit, for example, according to a sinc function. The radio frequency signal outputted from the amplitude modulation unit is amplified by the RF amplifier 32.

The management unit 34 controls the amplitudes and phases on the transmission channels independently of each other by controlling the transmit pulse generating unit 33.

Specifically, the management unit 34 controls the amplitude of the RF pulse inputted to each transmission channel so as to emit an RF magnetic field with a target amplitude based on a measurement result of the amplitude of the RF magnetic field received from the receiver unit 14 corresponding to each transmission channel. Also, the management unit 34 determines phase differences among the transmission channels based on measurement results of the phases of the RF magnetic fields received from the receiver unit 14. Then, based on the determined phase differences among the transmission channels, by controlling the transmit pulse generating unit 33, the management unit 34 controls the phase of the RF pulse to be inputted to each transmission channel such that the phase differences among the RF magnetic fields of the transmission channels will equal a target phase difference.

Consider a case in which, for example, a phase difference of 30 degrees is going to be established between the transmission channels CH1 and CH2. First, the management unit 34 inputs an appropriate RF pulse for the transmission channel CH1 and receives a measurement result of the RF magnetic field phase corresponding to the RF pulse from the receiver unit 14. Next, the management unit 34 inputs an RF pulse for the transmission channel CH2 thirty (30) degrees out of phase from the transmission channel CH1 and receives a measurement result of the phase of the RF magnetic field corresponding to the RF pulse from the receiver unit 14.

Then, the management unit 34 determines the phase difference between the measured RF magnetic fields and adjusts the phase of the RF pulse to be inputted to transmission channel CH2 such that a phase difference between the RF magnetic fields to be measured will approach 30 degrees based on a difference of the phase difference between the measured RF magnetic fields from the desired phase difference of 30 degrees.

The receiver unit 14 includes an MR signal generating unit configured to generate MR signal data based on the RF magnetic fields detected by the receiver coil 16 and transmits the generated MR signal data to the computer system 200 via the sequence control unit 15.

The receiver coil 16 receives the RF pulse upon RF pulse input to the transmission channel. Strength of an RF magnetic field from the transmitter coil may sometimes be too great for the receiver coil 16 to receive directly. Therefore, the management unit 34 puts the receiver coil 16 in a decoupled (very weakly coupled) state to prevent breakage of the receiver coil 16. Even in a weakly coupled state, the receiver coil 16 produces a slight output in response to the received RF magnetic field. Using the slight output, the receiver unit 14 measures the amplitude and phase of the RF magnetic field.

Note that since the receiver coil 16 receives the RF pulse upon RF pulse input to the transmission channel, a receive-only coil is preferable. That is, although it is not preferable that the transmitter coil to which an RF pulse is inputted will combine the receiver coil according to the present embodiment, there is no problem in using a combined transmitter-receiver coil to which no RF pulse is inputted, as the receiver coil according to the present embodiment. Also, preferably the receiver coil 16 which receives the RF pulse upon RF pulse input to the transmission channel is mounted on the object P.

Figure 3:
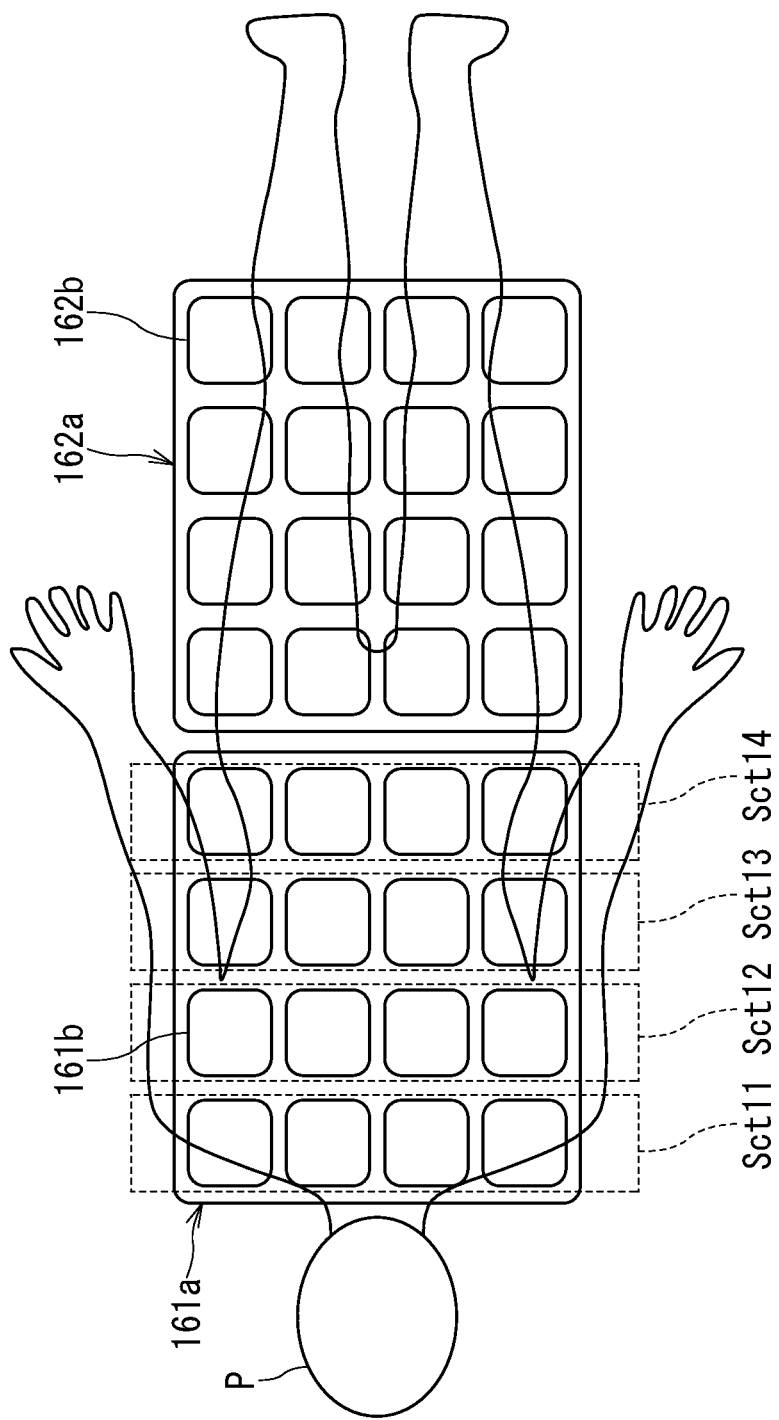
FIG. 3 is diagram showing a configuration example of phased array coils.

FIG. 3 is diagram showing a configuration example of phased array coils 161*a* and 162*a*. FIG. 3 shows an example in which two phased array coils 161*a* and 162*a* are mounted on the object P.

For example, some or all of plural coil elements 161*b* or 162*b* forming the phased array coil 161*a* or 162*a* mounted on the object P can be used as the receiver coil 16 which receives the RF pulse upon RF pulse input to the transmission channel.

In the example shown in FIG. 3, each of the phased array coils 161*a* and 162*a* is made up of 4×4=16 coil elements 161*b* or 162*b*. In the following description, it is assumed by way of example that some of the plural coil elements 161*b* making up the phased array coil 161*a* are used as the receiver coil 16 which receives the RF pulse upon RF pulse input to the transmission channel. Coil element groups each made up of four coil elements 161*b* arranged in a width direction of the object P will be referred to as coil sections Sct11, Sct12, Sct13, and Sct14, respectively.

The receiver coil 16 is set in units of coil elements, coil sections, or receiver channels either automatically or by the user. Here, it is assumed that distributed compositions such as in-phase composition, phase-reversal composition, QD composition, and anti-QD composition are applied to outputs of the respective coil elements and that outputs of the distributed compositions are connected to different receiver channels. Specifically, a distributed composition unit (not shown) of the receiver unit 14 combines or switches MR signals received from the coil elements 161*b* and 162*b* or the RF coil 130 and outputs resulting signals to corresponding reception-related circuits (receiver channels). That is, the receiver unit 14 is configured to be able to create sensitivity distributions of various imaging regions using desired plural coil elements 161*b* and 162*b* and thereby receive MR signals from the various imaging regions.

When phased array coils are used, the coil (hereinafter referred to as an imaging coil, as appropriate) used to receive MR data for imaging and the receiver coil 16 (hereinafter referred to as an amplitude/phase measurement coil, as appropriate) which receives the RF pulse upon RF pulse input to the transmission channel may be either the same or different. Also, when phased array coils are used, at least one of the imaging coil and amplitude/phase measurement coil may be selected by the user via the input unit 220.

In the following description, it is assumed that the receiver coil 16 means the amplitude/phase measurement coil in a strict sense. Naturally, when the imaging coil and amplitude/phase measurement coil are the same, the receiver coil 16 combines the imaging coil.

Now, consider an example of a case in which the user sets sections Sct12 and Sct13 as imaging coils via the input unit 220. In so doing, of course, the user may select the imaging coils by selecting receiver channels. In this example, the amplitude/phase control unit 31 may set sections Sct12 and Sct13 for the receiver coil 16 (amplitude/phase measurement coil). Also, the imaging coils may be set automatically according to a target imaging region set by the user.

Also, the imaging coil and amplitude/phase measurement coil may be different from each other. In this example, as the amplitude/phase measurement coil, the amplitude/phase control unit 31 may automatically set other sections Sct11 and Sct14 of the same phased array coil 161*a*, automatically set sections Sct11 and Sct12 so as to partially overlap the imaging coil, or automatically set sections Sct11, Sct12, Sct13, and Sct14 so as to totally overlap the imaging coil. Also, in this example, the receiver coil 16 (amplitude/phase measurement coil) may be further set manually by the user via the input unit 220 rather than set automatically.

On the other hand, only the receiver coil 16 (amplitude/phase measurement coil) may be set by the user. For example, when sections Sct12 and Sct13 are set as the receiver coil 16 (amplitude/phase measurement coil) by the user via the input unit 220 while the imaging coil remains yet not to be set, the same sections Sct12 and Sct13 as the amplitude/phase measurement coil may be set as the imaging coil by the amplitude/phase control unit 31 or the imaging coil may be set so as to partially or totally overlap the amplitude/phase measurement coil as with the above example.

Also, the receiver unit 14 measures the amplitude and phase of the RF magnetic field detected by the receiver coil 16 and provides results to the amplitude/phase control unit 31.

Specifically, the receiver unit 14 includes an MR signal processing unit 41. The MR signal processing unit 41 in turn includes a detection signal generating unit 42, a mixer 43, and an amplitude/phase measuring unit 44 in addition to the MR signal generating unit.

Figure 4:
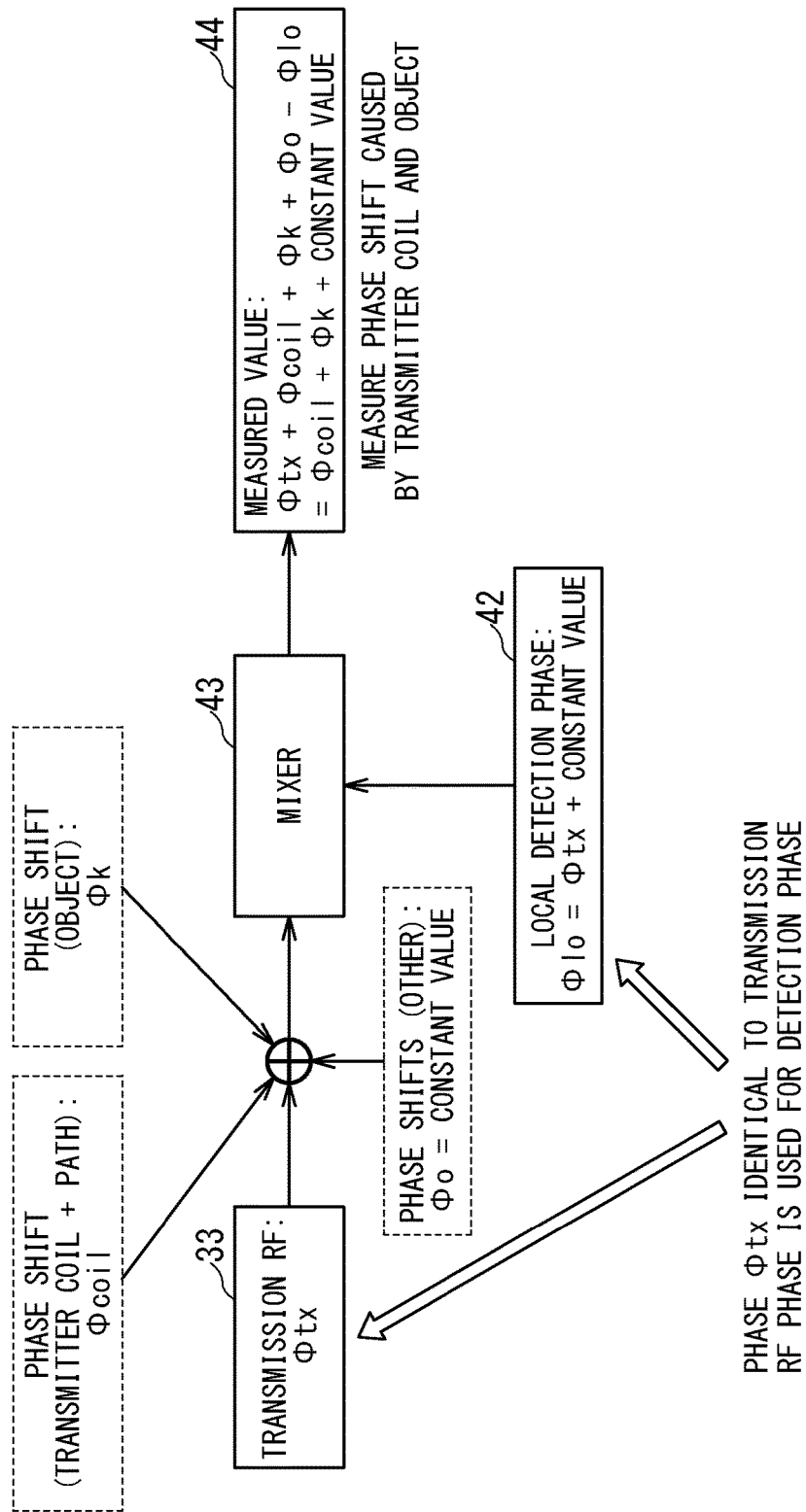
FIG. 4 is a conceptual diagram for describing components included in the phase of an RF magnetic field measured by the receiver unit.

FIG. 4 is a conceptual diagram for describing components included in the phase of an RF magnetic field measured by the receiver unit 14.

The detection signal generating unit 42 generates a local detection signal $\Phi$lo which has a same phase component as a phase component $\Phi$tx of the RF pulse generated by the transmit pulse generating unit 33.

The mixer 43 outputs a difference between an RF magnetic field detected by the receiver coil 16 and a local detection signal, the RF magnetic field corresponding to an RF pulse $\Phi$tx inputted to a transmission channel.

Under the control of the management unit 34, the amplitude/phase measuring unit 44 measures the amplitude and phase of the RF magnetic field detected by the receiver coil 16 and provides the results to the amplitude/phase control unit 31.

Based on the amplitudes and phases on respective transmission channels received from the amplitude/phase measuring unit 44, the management unit 34 of the amplitude/phase control unit 31 controls the amplitudes and phases of the RF pulses inputted to the respective transmission channels such that the amplitudes of the RF magnetic fields emitted from the respective transmission channels will equal respective target amplitudes and that the phase differences among the transmission channels will equal a target phase difference.

Also, the amplitude/phase control unit 31 and MR signal processing unit 41 may control the amplitudes and phases of the RF pulses and measure the amplitudes and phases of the RF magnetic fields during pre-scanning or main scanning of the object P, during installation of MRI apparatus 1, during a routine inspection, or during maintenance work. If the control and measurement are performed during pre-scanning or main scanning, the phase differences among the RF pulses transmitted from the transmitter unit 13 to the RF coil 130 may be corrected dynamically. The measured amplitude and phase on each transmission channel can be displayed on the display unit 230, allowing the user to easily understand current conditions and supporting the user in giving commands concerning the amplitude and phase via the input unit 220.

Incidentally, the target amplitudes and target phase differences stored beforehand in a storage unit (not shown) of the amplitude/phase control unit 31 or in the storage unit 250 of the computer system 200 may be used, specified by the user via the input unit 220, or provided via a network.

Also, to maintain repeatability of amplitude and phase measurement, the management unit 34 controls a time at which the radio frequency pulse is inputted to each of the plural transmission channels and a time at which the phase is measured by the MR signal processing unit 41 such that a time difference between a time at which the radio frequency magnetic field is emitted and a time at which the radio frequency magnetic field is measured through the receiver coil 16 will be constant on each of the plural transmission channels. The local detection signal $\Phi$lo has the same phase component as the phase component $\Phi$tx of the RF pulse generated by the transmit pulse generating unit 33. Consequently, an offset occurring at the time of measurement by the amplitude/phase measuring unit 44 can be equalized among different measurements, making it possible maintain repeatability of measurement.

Thus, even when measurements on different transmission channels are taken at different times such as taking measurements first on transmission channel CH1 and then on transmission channel CH2, for example, data can be compared among different measurements.

As shown in FIG. 4, the phase of the RF magnetic field detected by the receiver coil 16 is a sum of the phase $\Phi$tx of the RF pulse inputted to a transmission channel, a phase shift $\Phi$coil caused by a transmitter coil and a transmission path of the RF signal, a phase shift $\Phi$k corresponding to an impedance change caused by the presence of the object P, and other phase shifts $\Phi$0.

Thus, as shown in FIG. 4, the phase of a signal outputted from the mixer 43 is "$\Phi$coil+$\Phi$k+constant value", reflecting all of the transmitter coil, the transmit signal transmission path, and the impedance of the object P.

Also, the MR signal processing unit 41 includes an MR signal generating unit configured to generate MR signal data and transmits the generated MR signal data to the computer system 200 via the sequence control unit 15. Note that the receiver unit 14 may be installed on the side of a gantry apparatus equipped with the static magnet 110 and gradient coil 120 and the like.

Note that functions of the transmitter unit 13 of the management unit 34 and the amplitude/phase measuring unit 44 may be implemented by a CPU of a computer according to a transmission control program stored in a storage medium such as a ROM of the computer. In that case, the computer system 200 may be used as the computer and the control unit 260 may be used as the CPU of the computer.

The sequence control unit 15 scans the object P by driving the gradient power supply 11, transmitter unit 13, and receiver unit 14 based on sequence information transmitted from the computer system 200. After scanning the object P by driving the gradient power supply 11, transmitter unit 13, and receiver unit 14, when MR signal data is transmitted from the receiver unit 14, the sequence control unit 15 transfers the MR signal data to the computer system 200.

The sequence information defines procedures for scanning in time series, including intensity and timing with which the gradient power supply 11 supplies power to the gradient coil 120, intensity and timing with which the transmitter unit 13 transmits a radio frequency signal to the RF coil 130, timing with which the receiver unit 14 detects an MR signal, and the like.

The amplitudes and phases of the RF pulses transmitted by the transmitter unit 13 may also be controlled by the computer system 200. In that case, the control unit 260 of the computer system 200 functions at least as the management unit 34 and amplitude/phase measuring unit 44 according to the transmission control program. For example, when the phase differences among the RF pulses transmitted from the transmitter unit 13 to the RF coil 130 are corrected dynamically during pre-scanning or main scanning of the object P, the amplitudes and phases of the RF pulses transmitted by the transmitter unit 13 may be controlled by the computer system 200 via the sequence control unit 15.

Next, exemplary operation of the magnetic resonance imaging apparatus 1 and transmission control method according to the present embodiment will be described.

The amplitudes and phases of the RF pulses may be corrected by the amplitude/phase control unit 31 during pre-scanning or main scanning or at other times. First, description will be given of an example of procedures for correcting the amplitudes and phases of RF pulses separately from pre-scanning and main scanning.

Figure 5:
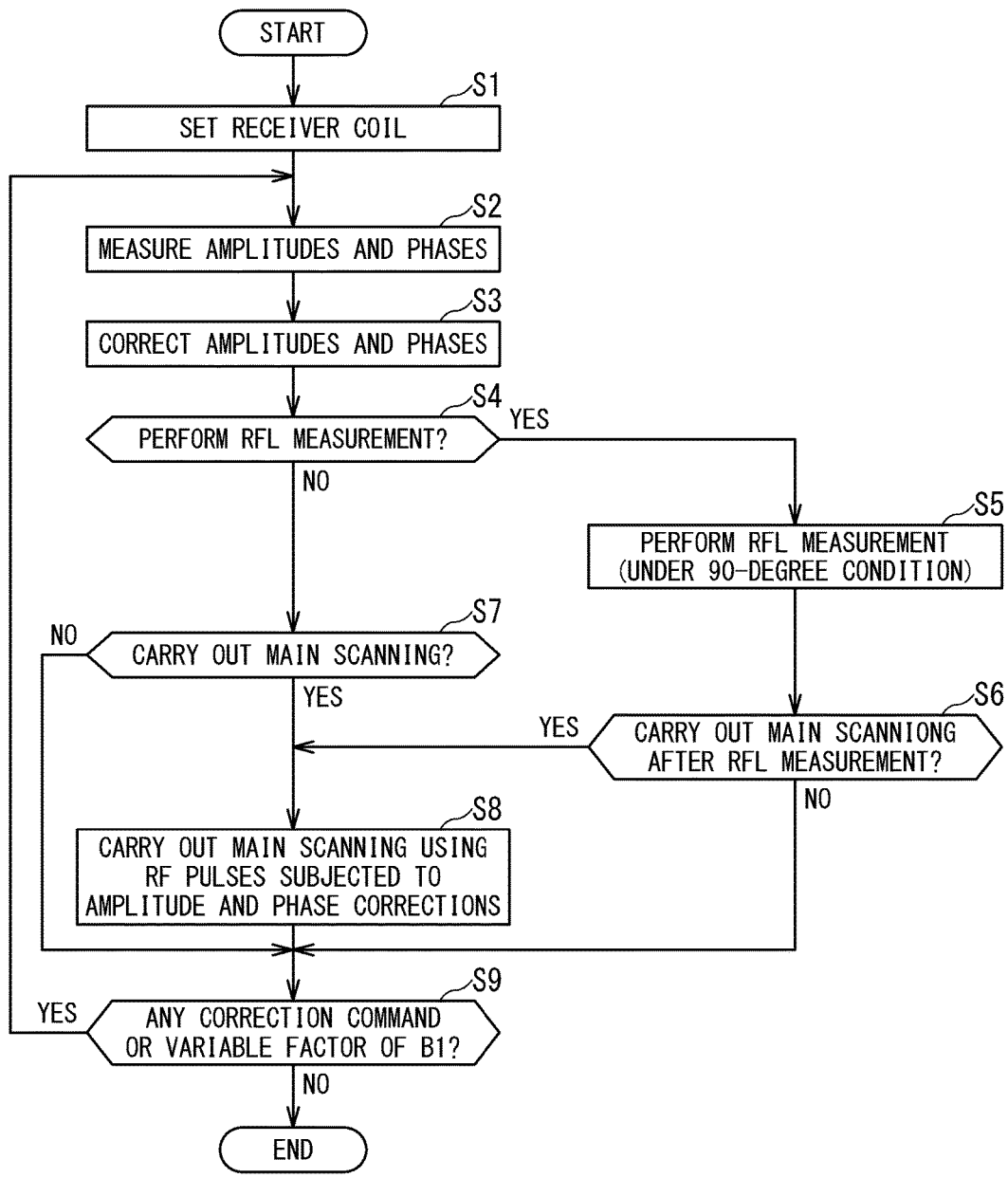
FIG. 5 is a flowchart showing an example of procedures for correcting the amplitudes and phases of RF pulses separately from pre-scanning and main scanning based on amplitude and phase measurements.

FIG. 5 is a flowchart showing an example of procedures for correcting the amplitudes and phases of RF pulses separately from pre-scanning and main scanning based on amplitude and phase measurements.

When the amplitudes and phases of RF pulses are corrected before pre-scanning and main scanning are carried out, a target amplitude and phase are preset from the RF pulse inputted to each transmission channel by performing amplitude and phase measurements as pre-scanning in advance, for example, as shown in FIG. 5. For example, when pre-scanning (e.g., measurement of RF power (RF level, which hereinafter is referred to as RFL) etc.) is carried out in which the amplitude difference and phase difference between transmission channels are important, desirably a target amplitude and phase are preset from the RF pulse inputted to each transmission channel by performing amplitude and phase measurements as pre-scanning before the pre-scanning for RFL measurement.

The procedures shown in FIG. 5 are started when a command to start pre-scanning or main scanning is given by the user via the input unit 220. In the following description, it is assumed by way of example that the receiver coil 16 is made up of some of the plural coil elements 161*b* making up the phased array coil 161*a*.

First, in step S1, the amplitude/phase control unit 31 sets the receiver coil 16 according to a command given by the user via the input unit 220 or according to details of scanning specified by a scan start command from the user. Also, if the scanning specified by the scan start command is main scanning or the like which involves image generation, the amplitude/phase control unit 31 sets a coil which is the same as or different from the receiver coil 16 as the imaging coil according on a command given by the user via the input unit 220 or according to details of scanning specified by the scan start command from the user.

Next, in step S2, amplitude and phase measurement is performed as pre-scanning. Specifically, the amplitude/phase control unit 31 inputs an RF pulse having a predetermined amplitude and phase to each transmission channel. The receiver coil 16 in a decoupled state detects the RF magnetic field corresponding to the RF pulse and outputs a signal corresponding to the detected RF magnetic field. Then, the MR signal processing unit 41 measures the amplitude and phase based on the output from the receiver coil 16. Advisably, measurements on each transmission channel are performed in order.

Next, based on measurement results of the amplitudes and phases, the amplitude/phase control unit 31 corrects the amplitudes and phases of the RF pulses such that the phase differences among the transmission channels will approach a target phase difference (step S3). As a result, the RF pulse inputted to each transmission channel from the amplitude/phase control unit 31 has had the amplitude and phase difference of the corresponding RF magnetic field corrected so as to approach target values.

Next, in step S4, it is determined whether the amplitude/phase control unit 31 should perform RFL measurement. When step S3 is carried out for the first time, the determination is made based on details of the scan start command received at the start of the procedures. On the other hand, after a return from step S9, the determination is made based on details of a correction command given in step S9. In either case, if it has been specified beforehand that pre-scanning for RFL measurement be carried out after step S3, the flow goes to step S5. If pre-scanning for RFL measurement needs to be carried out, the flow goes to step S5. On the other hand, if there is no need to carry out pre-scanning for RFL measurement, the flow goes to step S7.

Next, in step S5, the sequence control unit 15 performs pre-scanning (e.g., RFL measurement) in which the amplitude difference and phase difference between transmission channels are important.

In this way, if measurement of the RF pulse amplitudes and phases is incorporated into the pre-scanning before carrying out the pre-scanning in which the amplitude difference and phase difference between transmission channels are important, more accurate pre-scanning results can be obtained by correcting the amplitudes and phases of the RF pulses beforehand.

Next, in step S6, based on the details of the scan start command received at the start of the procedures, the sequence control unit 15 determines whether to carry out main scanning. If main scanning is to be carried out, the flow goes to step S8. On the other hand, if there is no need to carry out main scanning, the flow goes to step S9.

On the other hand, if it is determined in step S4 that there is no need to carry out pre-scanning for RFL measurement, the sequence control unit 15 determines in step S7 whether main scanning is to be carried out, based on the details of the scan start command received at the start of the procedures. If main scanning is to be carried out, the flow goes to step S8. On the other hand, if there is no need to carry out main scanning, the flow goes to step S9.

Next, in step S8, using the imaging coil set by the amplitude/phase control unit 31 in step S1, the sequence control unit 15 carries out main scanning by inputting the RF pulses whose amplitudes and phases have been corrected in step S3 to the respective transmission channels.

Next, in step S9, the control unit 260 determines whether a command to correct the amplitude and phase of the RF pulse to be inputted to each transmission channel again has been given by the user or whether a command to continue scanning has been given and whether there is any variable factor of B1. Possible variable factors of B1 include, for example, a change in a set value (target value) of the amplitude or phase of any RF magnetic field for scans carried out successively from a current value, a change of coil, a change in a target imaging region, and the like.

If a command to correct the amplitude and phase of the RF pulse to be inputted to each transmission channel again has been given by the user or if a command to continue scanning has been given and there is a variable factor of B1, the flow returns to step S2. On the other hand, if a command to correct the amplitude and phase of the RF pulse to be inputted to each transmission channel again has not been given by the user and if a command to continue scanning has not been given or there is no variable factor of B1, a series of procedures is finished.

If the flow returns from step S9 to step S2 in response to a user command to correct the amplitude and phase of the RF pulse to be inputted to each transmission channel again and if there is a variable factor of B1, it is often the case that the RF level has changed as well, and thus preferably pre-scanning (step S5) for RFL measurement is carried out.

Through the above procedures, pre-scanning and main scanning can be carried out using the corrected amplitudes and phases of the RF pulses.

Advisably, the RF pulse given to each transmission channel for measurement in step S2 is a continuous wave or square wave. If k-space is filled with a uniform frequency and phase using a continuous wave or square wave, higher accuracy can be achieved by short-time measurements.

When the flow returns from step S9 to step S2, if there is no change in conditions of the B1 magnetic fields (e.g., if there is a user command to correct the amplitude and phase of the RF pulse to be inputted to each transmission channel again), measurement results of the amplitudes and phases in step S2 can be used for purposes of verifying the RF magnetic fields generated by the corrected amplitudes and phases of the RF pulses. Therefore, even when the determination in step S9 is NO, the amplitude and phase measurement in step S2 may be carried out in order to observe the RF magnetic fields generated by the corrected amplitudes and phases of the RF pulses.

Next, description will be given of an example of procedures for correcting the amplitudes and phases of RF pulses during pre-scanning or main scanning.

Figure 6:
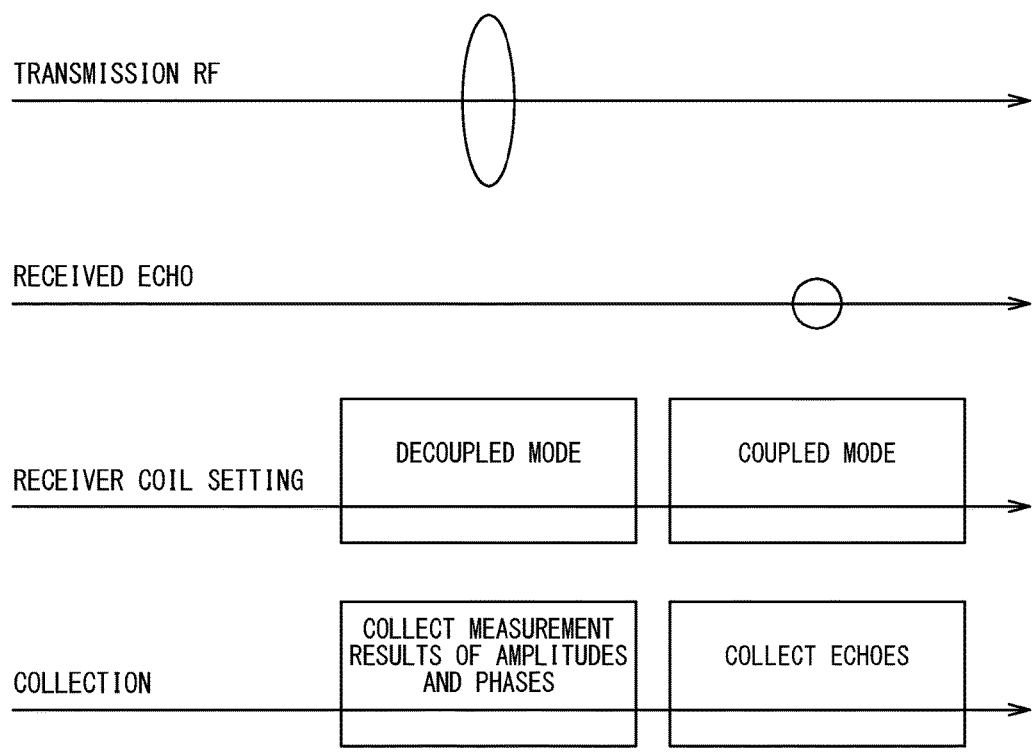
FIG. 6 is timing chart showing an example of procedures for performing amplitude and phase measurement during main scanning.

FIG. 6 is timing chart showing an example of procedures for performing amplitude and phase measurement during main scanning.

When an RF magnetic field is radiated, the receiver coil 16 in a decoupled state outputs a signal corresponding to the RF magnetic field. The MR signal processing unit 41 measures the amplitude and phase of the RF magnetic field according to the output of the receiver coil 16, and provides results to the amplitude/phase control unit 31.

Subsequently, under the control of the management unit 34, the receiver coil 16 shifts to a coupled state and receives a received echo from the object P. The MR signal processing unit 41 generates an MR signal according to the received echo received by the receiver coil 16.

As shown in FIG. 6, even during main scanning or pre-scanning, since the RF magnetic field is received directly by the receiver coil 16 (preferably in a decoupled mode) upon transmission of the RF magnetic field, usual collection of received echo data and measurement of amplitudes and phases are allowed to coexist.

The MRI apparatus 1 according to the present embodiment has plural transmission channels and allows the amplitude and phase of the RF pulse inputted to each transmission channel to be adjusted accurately with a hardware configuration similar to that of conventional MRI apparatus without using a pickup coil. This makes it possible to optimize the RF magnetic field (B1) emitted from each transmission channel.

Also, MRI apparatus 1 allows the amplitudes and phases of RF pulses to be adjusted by taking into consideration the influence of all the transmission paths of RF pulses and as well as the influence of the object P.

Also, since measurement and control of amplitudes and phases can be performed in a simple and easy manner, corrections can be made easily even if there are phase shifts and the like under the influence of aging-related equipment deterioration. Thus, by performing measurement and control of amplitudes and phases according to the present embodiment, for example, during an annual routine inspection, the influence of aging-related deterioration can be corrected extremely easily and precisely.

Also, since the amplitude and phase of the RF magnetic field emitted from each transmission channel can be measured and corrected, there is no need to make precise coil adjustments to prevent phase shifts.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
   a receiver coil configured to receive a radio frequency (RF) magnetic field emitted from a transmitter coil while an RF pulse is supplied to the transmitter coil even though the receiver coil is in a de-coupled state from the transmitter coil; and
   at least one processing circuitry configured to process at least one of an amplitude and a phase of the RF magnetic field based on an output from the de-coupled receiver coil while the RF pulse is being supplied to the transmitter coil.

2. The apparatus according to claim 1, wherein
   the at least one processing circuitry is further configured to control at least one of an amplitude and a phase of the RF pulse supplied to the transmitter coil based on at least one of the processed amplitude and the processed phase of the RF magnetic field.

3. The apparatus according to claim 2, wherein
   the at least one processing circuitry is further configured to put the receiver coil in a coupled state while the receiver coil receives an MR signal from an object upon elapse of a predetermined time after the transmitter coil emits the RF magnetic field.

4. A magnetic resonance imaging (MRI) radio frequency (RF) transmission control method comprising:
   receiving, via an RF coil, a magnetic field emitted from an RF transmitter coil while an RF pulse is supplied to the RF transmitter coil even though the receiver coil is in a de-coupled state from the transmitter coil; and
   processing, using at least one processing circuitry, at least one of an amplitude and a phase of the RF magnetic field based on an output from the de-coupled RF receiver coil while the RF pulse is being supplied to the transmitter coil.

5. The method according to claim 4, further comprising controlling at least one of an amplitude and a phase of the RF pulse supplied to the RF transmitter coil based on at least one of the processed amplitude and the measured phase of the RF magnetic field.

6. The method according to claim 5, further comprising putting the receiver coil in a coupled state while the RF receiver coil receives an MR signal from an object upon elapse of a predetermined time after the RF transmitter coil emits the RF magnetic field.

* * * * *